(12) United States Patent
O'Brien et al.

(10) Patent No.: US 11,448,717 B2
(45) Date of Patent: Sep. 20, 2022

(54) METHOD AND DEEP QUANTITATIVE SUSCEPTIBILITY MAPPING (QSM)

(71) Applicant: Siemens Healthcare GmbH, Erlangen (DE)

(72) Inventors: Kieran O'Brien, Highgate Hill (AU); Markus Barth, St. Lucia (AU); Steffen Bollmann, Dutton Park (AU)

(73) Assignee: Siemens Healthcare GmbH, Erlangen (DE)

(*) Notice: Subject to any disclaimer, the term of this patent is extended or adjusted under 35 U.S.C. 154(b) by 935 days.

(21) Appl. No.: 16/236,791

(22) Filed: Dec. 31, 2018

(65) Prior Publication Data

US 2019/0204401 A1 Jul. 4, 2019

Related U.S. Application Data

(60) Provisional application No. 62/611,687, filed on Dec. 29, 2017.

(51) Int. Cl.
*G01R 33/56* (2006.01)
*G01R 33/44* (2006.01)
(Continued)

(52) U.S. Cl.
CPC ......... *G01R 33/5608* (2013.01); *G01R 33/24* (2013.01); *G01R 33/443* (2013.01);
(Continued)

(58) Field of Classification Search
CPC .. G01R 33/5608; G01R 33/24; G01R 33/443; G16H 30/40; G06N 3/04; G06N 3/08;
(Continued)

(56) References Cited

U.S. PATENT DOCUMENTS 9,370,316 B2 * 6/2016 Ewing .................. A61B 5/7267
9,395,425 B2 * 7/2016 Diamond ............. A61B 5/0042
(Continued)

FOREIGN PATENT DOCUMENTS

WO 2016209930 A1 12/2016

OTHER PUBLICATIONS

Jung et al. "Overview of quantitative susceptibility mapping using deep learning—Current status, challenges and opportunities", Machine Learning and Deep Learning in Magnetic Resonance, 2020 (Year: 2020).*

(Continued)

*Primary Examiner* — Vu Le
*Assistant Examiner* — Julius Chai
(74) *Attorney, Agent, or Firm* — Banner & Witcoff Ltd.

(57) ABSTRACT

Techniques are disclosed to leverage the use of convolutional neural networks or similar machine learning algorithms to predict an underlying susceptibility distribution from MRI phase data, thereby solving the ill-posed inverse problem. These techniques include the use of Deep Quantitative Susceptibility "DeepQSM" mapping, which uses a large amount of simulated susceptibility distributions and computes phase distribution using a unique forward solution. These examples are then used to train a deep convolutional neuronal network to invert the ill-posed problem.

20 Claims, 13 Drawing Sheets

(7 of 13 Drawing Sheet(s) Filed in Color)

(51) Int. Cl.
*G06N 3/04* (2006.01)
*G06N 3/08* (2006.01)
*G16H 30/40* (2018.01)
*G06T 11/00* (2006.01)
*G06T 7/00* (2017.01)
*G01R 33/24* (2006.01)

(52) U.S. Cl.
CPC .............. *G06N 3/04* (2013.01); *G06N 3/08* (2013.01); *G06T 7/0012* (2013.01); *G06T 11/006* (2013.01); *G16H 30/40* (2018.01); *G06T 2207/10088* (2013.01); *G06T 2207/20081* (2013.01); *G06T 2207/20084* (2013.01); *G06T 2207/30016* (2013.01)

(58) Field of Classification Search
CPC .............. G06T 7/0012; G06T 11/006; G06T 2207/10088; G06T 2207/20081; G06T 2207/20084; G06T 2207/30016
See application file for complete search history.

(56) References Cited

U.S. PATENT DOCUMENTS

| | | | |
|---|---|---|---|
| 9,542,763 | B2 | 1/2017 | Bilgic et al. |
| 10,145,928 | B2* | 12/2018 | Liu .................. G01R 33/56536 |
| 2015/0145515 | A1* | 5/2015 | Liu ...................... G01R 33/243 |
| | | | 324/309 |
| 2015/0338492 | A1 | 11/2015 | Sato et al. |
| 2018/0180688 | A1 | 6/2018 | Koch et al. |
| 2018/0372826 | A1* | 12/2018 | Meineke ............ G01R 33/5601 |

OTHER PUBLICATIONS

Liu, Tian et al. "Morphology Enabled Dipole Inversion (MEDI) from a Single-Angle Acquisition: Comparison with COSMOS in Human Brain Imaging" Magnetic Resonance in Medicine; vol. 66; No. 3; pp. 777-783; (2011) // DOI: 10.1002/mrm.22816.

Jin, Kyong Hwan et al. "Deep Convolutional Neural Network for Inverse Problems in Imaging" IEEE Transactions on Image Processing, vol. 26, No. 9, pp. 4509-4522, Sep. 2017.

Shmueli, Karin et al. "Magnetic Susceptibility Mapping of Brain Tissue In Vivo Using MRI Phase Data" Magnetic Resonance in Medicine; vol. 62; No. 6; pp. 1510-1522; (2009) // DOI 10.1002/mrm.22135.

Langkammer, Christian et al. "Fast quantitative susceptibility mapping using 3D EPI and total generalized variation" NeuroImage; Elsevier, vol. 111; pp. 622-630; 2015 // http://dx.doi.org/10.1016/j.neuroimage.2015.02.041; DOI: 10.1016/j.neuroimage.2015.02.041.

Langkammer, Christian et al. "Quantitative Susceptibility Mapping: Report From the 2016 Reconstruction Challenge" Magnetic Resonance in Medicine; vol. 79; No. 3; pp. 1661-1673; (2018) // DOI: 10.1002/mrm.26830.

Abadi, Martin et al. "TensorFlow: Large-Scale Machine Learning on Heterogeneous Distributed Systems", arXiv:1603.04467 [cs.DC]; Mar. 2016.

Deistung, Andreas et al. "Toward in vivo histology: A comparison of quantitative susceptibility mapping (QSM) with magnitude-, phase-, and R2-imaging at ultra-high magnetic field strength" NeuroImage; vol. 65; pp. 299-314; (2013) //http://dx.doi.org/10.1016/j.neuroimage.2012.09.055.

Chen, Weiwei et al. "Intracranial Calcifications and Hemorrhages: Characterization with Quantitative Susceptibility Mapping" Radiology, vol. 270; No. 2, pp. 496-505; (2014).

Liu, Tian et al. "Calculation of Susceptibility Through Multiple Orientation Sampling (COSMOS): A Method for Conditioning the Inverse Problem From Measured Magnetic Field Map to Susceptibility Source Image in MRI" Magnetic Resonance in Medicine; vol. 61; pp. 196-204; 2009.

Ronneberger, Olaf et al. "U-Net: Convolutional Networks for Biomedical Image Segmentation" Medical Image Computing and Computer-Assisted Intervention (MICCAI), Springer, LNCS, vol. 9351, pp. 234-241, 2015 // arXiv:1505.04597 [cs.CV].

Li, Wei et al. "A method for estimating and removing streaking artifacts in quantitative susceptibility mapping" Neuroimage, vol. 108, pp. 111-122, Mar. 2015 //DOI: 10.1016/j.neuroimage.2014.12.043.

Chatnuntawech, Itthi et al. "Single-Step Quantitative Susceptibility Mapping with Variational Penalties" NMR in Biomedicine, vol. 30, No. 4, Apr. 2017 (Published online Jun. 22, 2016. doi: 10.1002/nbm.3570).

Li, Weii et al. "Differential Developmental Trajectories of Magnetic Susceptibility in Human Brain Gray and White Matter Over the Lifespan" Human Brain Mapping; vol. 35; No. 6; pp. 2698-2713; (2014) // DIO: 10.1002/hbm.22360.

Dong, Chao et al. "Compression Artifacts Reduction by a Deep Convolutional Network" ICCV, Proceedings of the IEEE International Conference on Computer Vision, pp. 576-584, (2015).

Bollmann, Steffen et al. "The Challenge of Bias-Free Coil Combination for Quantitative Susceptibility Mapping at Ultra-High Field" Magnetic Resonance in Medicine, vol. 79, No. 1, pp. 97-107, 2018 (First published: Mar. 1, 2017); DOI: 10.1002/mrm.26644; https://doi.org/10.1002/mrm.26644.

McCann, Michael T. et al. "A Review of Convolutional Neural Networks for Inverse Problems in Imaging" arXiv:1710.04011v1 [eess.IV], Oct. 2017.

Schweser, Ferdinand et al. "Foundations of MRI phase imaging and processing for Quantitative Susceptibility Mapping (QSM)" Zeitschrift für Medizinische Physik; vol. 26; No. 1; pp. 6-34; (2016) // DOI: 10.1016/j.zemedi.2015.10.002 https://doi.org/10.1016/j.zemedi.2015.10.002.

Deistung, Andreas et al. "Overview of quantitative susceptibility mapping" NMR in Biomedicine; vol. 30; 2017 // DOI: 10.1002/nbm.3569.

Golkov, Vladimir et al. "q-Space Deep Learning: Twelve-Fold Shorter and Model-Free Diffusion MRI Scans" IEEE Transactions on Medical Imaging, vol. 35, No. 5, pp. 1344-1351, May 2016 // XP011607959; ISSN: 0278-0062; DOI: 10.1109/TMI.2016.2551324.

Liu, Chunlei et al. "Susceptibility-Weighted Imaging and Quantitative Susceptibility Mapping in the Brain" Journal of Magnetic Resonance in Medicine; vol. 42; pp. 23-41; (2015) // DOI: 10.1002/jmri.24768.

* cited by examiner

METHOD AND DEEP QUANTITATIVE SUSCEPTIBILITY MAPPING (QSM)

CROSS-REFERENCE TO RELATED APPLICATIONS

The present application claims the benefit of the filing date of provisional application 62/611,687, filed on Dec. 29, 2017, the contents of which are incorporated herein by reference in their entirety.

TECHNICAL FIELD

The present invention concerns methods and devices for magnetic resonance imaging (MRI), and in particular to such methods and devices that use convolutional neural networks or similar machine learning algorithms to predict an underlying susceptibility distribution from MRI phase data to solve an ill-posed inverse problem.

BACKGROUND

Magnetic susceptibility describes a sample-induced magnetization when placed in a static magnetic field. Quantitative susceptibility mapping (QSM) aims to extract the magnetic susceptibility of tissue and includes a group of methods by which the absolute concentrations of iron, calcium, and other substances may be measured in tissues based on changes in local susceptibility. The measurement of tissue magnetic susceptibility using MRI is of high interest, because magnetic susceptibility contains valuable information about the chemical composition and microstructure of tissues. Moreover, it has potential to give new and unique, non-invasive insight into, for instance, neurodegenerative disease pathology and differentiation between different types of lesions in the brain.

QSM is a post-processing technique that computes the underlying magnetic susceptibility distribution of a sample from MRI phase measurements by solving an inverse problem. However, to compute the field-to-source-inversion, an ill-posed deconvolution from magnetic field to susceptibility source of the local tissues is required. Conventional solutions to solve the inverse problem are generally not clinically feasible, sacrifice fine structure information, and require data from multiple orientations, which is time consuming and processor intensive.

SUMMARY OF THE INVENTION

An object of the present invention is to leverage the use of convolutional neural networks or similar machine learning algorithms to predict an underlying susceptibility distribution from MRI phase data, thereby solving the ill-posed inverse problem. This object is achieved in accordance with the present invention via a "DeepQSM," technique, which uses a large amount of simulated susceptibility distributions and computes phase distribution using a unique forward solution. These examples are then used to train a deep convolutional neuronal network to invert the ill-posed problem.

An advantage of the technique realized in accordance with the aspects described herein is a fast, accurate, and robust solution of the QSM inversion using data associated with a single orientation. In particular, this new technique incorporates spatial structure into the regularization problem, and therefore delivers high quality reconstructions that do not suffer from issues associated with conventional methods, such as smoothing or noise amplification.

A further advantage of the aspects as described herein is that the proposed neural network approach is more robust to noise compared to conventional approaches such as the use of truncated k-space division (TKD).

Yet another advantage of the DeepQSM aspects described herein is that the reliance on smoothing regularization is reduced, which may potentially better preserve the fine structures within certain tissues (e.g., the brain) to produce more accurate and valuable diagnostic test data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
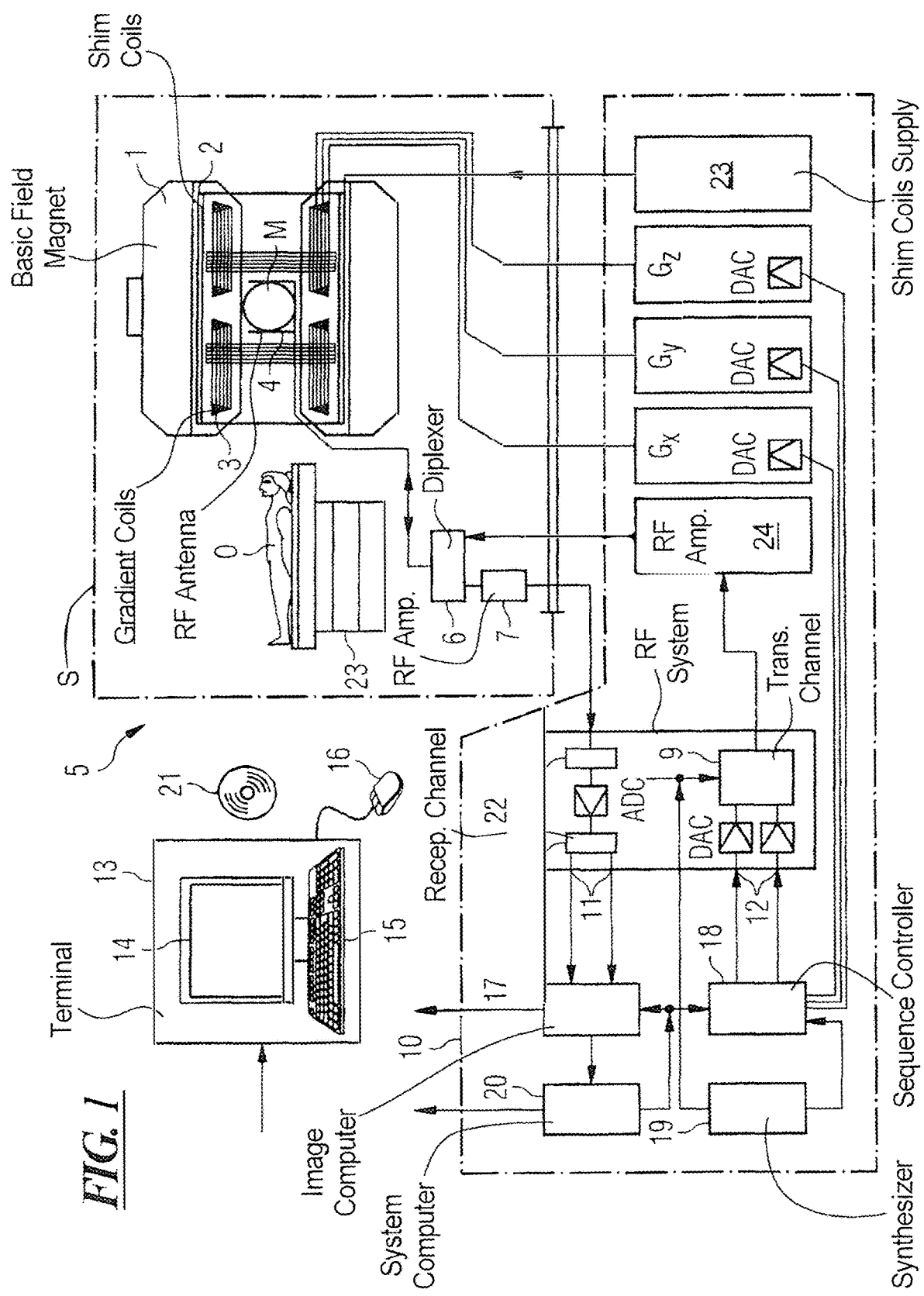
FIG. 1 is a block diagram of a magnetic resonance apparatus constructed and operating in accordance with the present aspects.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 23 for the shim-coils 2.

A cylindrically shaped gradient coil system 3 is incorporated in the basic field magnet 1, composed of three windings. Each winding is supplied by a corresponding amplifier Gx, Gy and Gz, with power for generating a linear gradient field in a respective axis of a Cartesian coordinate system. The first partial winding of the gradient field system 3 generates a gradient Gx in the x-axis, the second partial winding generates a gradient Gy in the y-axis, and the third partial winding generates a gradient Gz in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier 24 into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner, which includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen. The components within the dot-dash outline S are commonly called a magnetic resonance scanner.

Thus, the magnetic resonance apparatus 5 as shown in FIG. 1 may include various components to facilitate the measurement, collection, and storage of MRI image data and/or MRI phase data. Again, this MRI phase data may then be utilized in accordance with convolutional neural networks or similar machine learning algorithms to predict the underlying susceptibility distribution, thereby solving the ill-posed inverse problem.

Traditional techniques to solve the ill-posed inverse problem include the so-called "COSMOS" method, which is a known technique described, for instance, in Liu et al. "Calculation of susceptibility through multiple orientation sampling (COSMOS): A method for conditioning the inverse problem from measured magnetic field map to susceptibility source image in MRI", Magn. Reson. Med. 61, 196-204 (2009). The COSMOS method uses signal phase obtained from multiple orientations to condition the inverse problem, but is not clinically feasible due to time constraints and patient discomfort.

Other conventional methods include the truncated k-space division (TKD), morphology enabled dipole inversion (MEDI), total generalized variation (TGV), single-step QSM (SS-QSM) or sparse linear equation and least-squares algorithms (LSQR). These methods exist to solve the inverse problem in single orientation 3D phase data. However, the resulting images often show a significant amount of smoothing due to the regularizations applied, thus sacrificing fine structure information.

Figure 2:
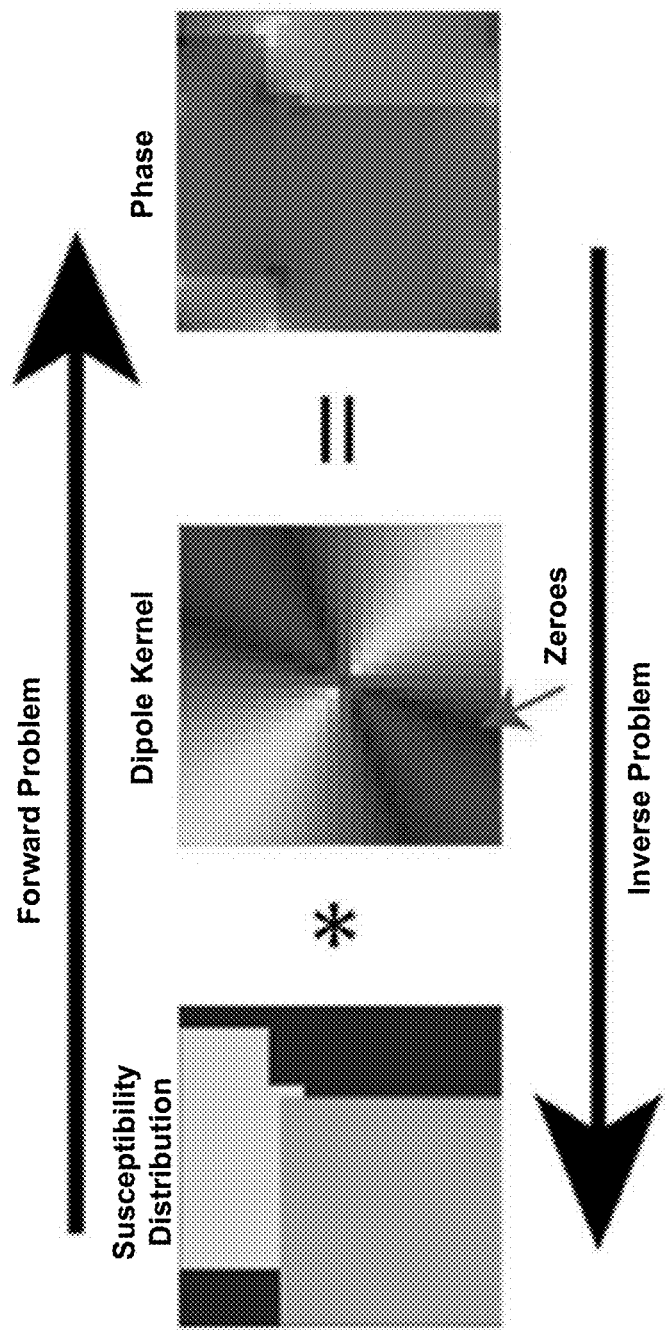
FIG. 2 is a graphical illustration of the forward and inverse problem, in accordance with an aspect of the disclosure.
Figure 3:
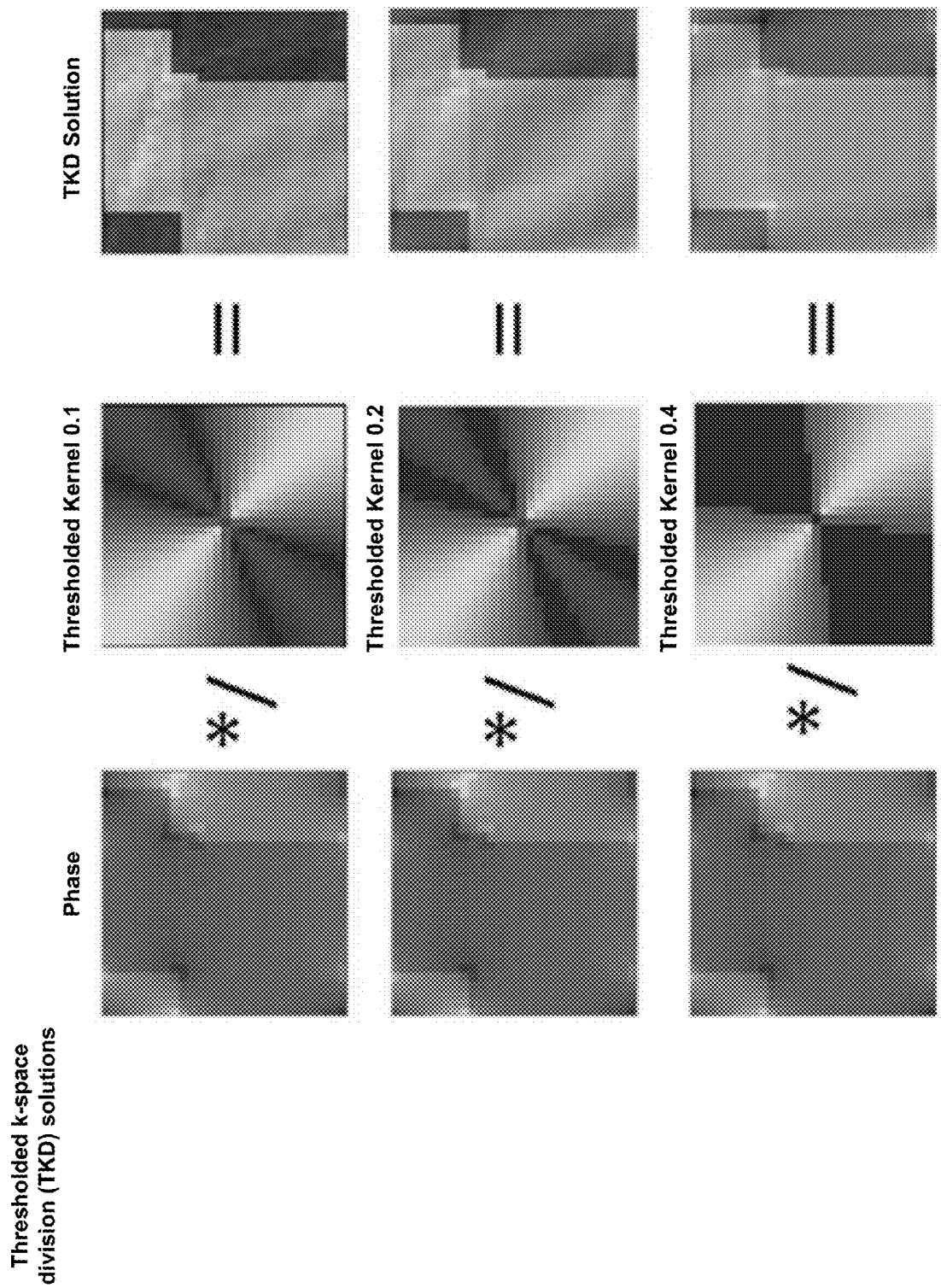
FIG. 3 is a graphical illustration of thresholded k-space division (TKD) solutions and the influence of different thresholds on the QSM solution, in accordance an aspect of the disclosure.

The inverse problem of QSM is said to be "μl-posed," because the dipole kernel contains zeros on two conic surfaces and small values close to these cones. This issue is illustrated in further detail in FIGS. 2-3. As a result, this leads to multiple possible susceptibility distributions that could account for the measured field. Again, the current practice to overcome this ill-posed problem is to either acquire multiple orientations, which is time consuming because additional MRI phase measurements are necessary, or to regularize the inversion.

Moreover, multi-orientation techniques are clinically not applicable, as such techniques require the patient to rotate in the scanner, and even less process-intensive techniques (e.g., COSMOS) require at least 3 orientations. These techniques generally rely on the fact that the magic angle cone follows the rotation of the object in the scanner and the zero cone surfaces do not intercept, leading to an overdetermined field-to-susceptibility problem. As a result, conventional techniques such as COSMOS do not take into account microstructural anisotropy effects. To remedy this issue, more sophisticated techniques that require 6 orientations (STI, "susceptibility tensor imaging") or 12 (GLTA, "generalized lorentzian tensor approach") have been developed.

With regards to the single orientation techniques that are clinically feasible, these are generally subdivided into two categories. The first of these categories are known as non-iterative k-space techniques and include techniques such as TKD and superfast dipole inversion (SDI). Thresholded k-space division (TKD) uses a modified dipole kernel in which small values are replaced by a constant. Although this leads to a solution without streaking artifacts, the resultant magnetic susceptibility values are systematically underestimated, and there is no universal way of robustly defining the value of this constant due its dependence on the noise level in the data.

The second of these categories are known as iterative strategies in image space and include techniques such as MEDI, HEIDI ("Homogeneity Enabled Incremental Dipole Inversion"), and iLSQR ("iterative LSQR"). These techniques are based on the minimization of the L2 norm between the measured magnetic field and the field generated by convolving the dipole with the magnetic susceptibility distribution using standard optimization techniques (e.g., conjugate gradient, steepest descent). These techniques can also include prior information based on the underlying tissue structure (e.g., as is the case in MEDI) or sparsity assumptions.

The aforementioned inversion problem cannot be solved analytically if only a single orientation is acquired and is therefore ill-posed. To remedy this issue, and to address the shortcomings of the conventional systems described above, the aspects described herein recognize that the forward problem, in contrast, relates susceptibility information to phase, and is uniquely defined and can be computed in a straightforward convolution operation with a dipole kernel. In the aspects described in further detail below, large amounts of examples may be generated linking the forward problem to the inverse problem. The aspects described herein leverage various computing architectures, such as neural networks, for example, that utilize these large amounts of examples as training data to learn an underlying model, which is then used to solve the aforementioned ill-posed inverse problem.

To do so, the aspects further described herein may implement methods that utilize machine learning concepts (e.g., deep convolutional neural networks), to solve the inverse problem. This solution may be based on, for instance, a data driven regularization that takes structural information into account and thus avoids current problems associated with conventional regularization techniques in the field. In doing so, the aspects described herein deliver an accurate and fast solution to the ill-posed QSM inverse problem based on single orientation data, and thus overcome the current fundamental limitations with regards to the clinical application of QSM.

The aspects described herein utilize a technique referred to as "DeepQSM." Again, these DeepQSM techniques utilize a large amount of simulated susceptibility distributions, which are then used to compute the phase distribution using the unique forward solution. These sets of simulated susceptibility distributions, along with their corresponding phase distributions, are then established as examples that may then be used to train a machine learning model (e.g., a deep convolutional neuronal network). This model may, in turn, be used to invert the ill-posed problem. An illustration of the steps and examples are illustrated in FIGS. 4-5.

Figure 4:
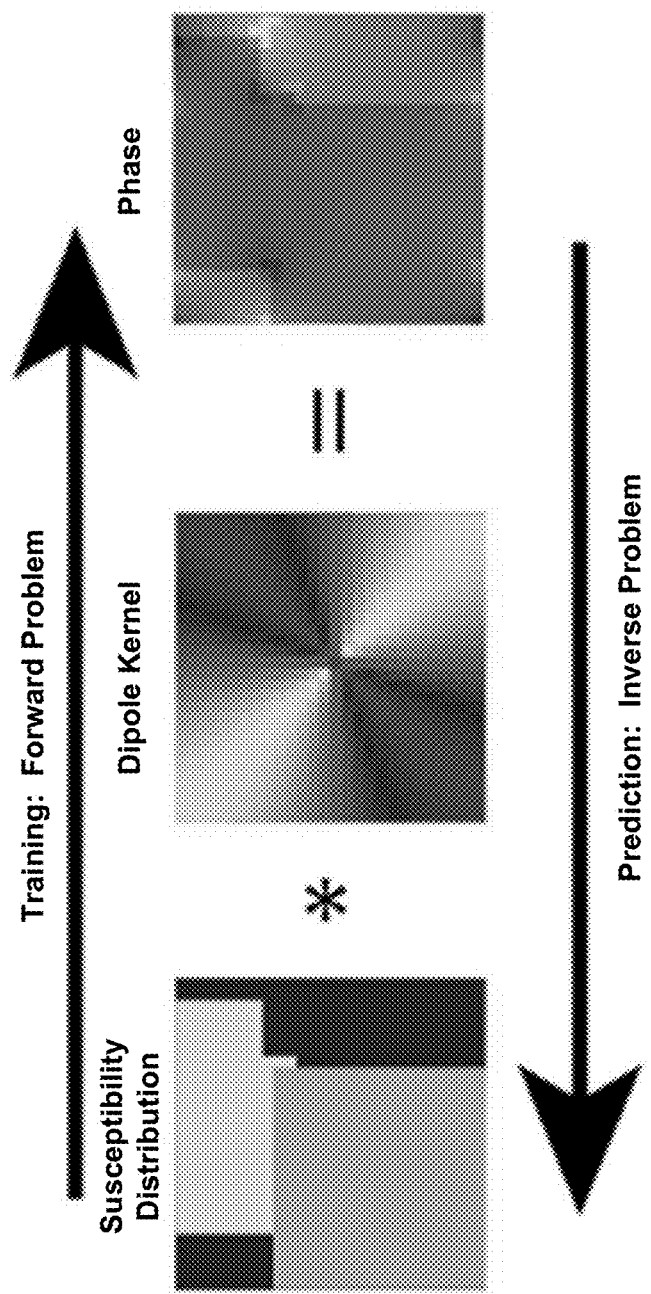
FIG. 4 is a graphical illustration of the training and prediction phase in DeepQSM, in accordance with an aspect of the disclosure.

For example, FIG. 4 illustrates a susceptibility distribution that is convolved with a dipole kernel to yield a corresponding phase distribution as part of a training step to solve the forward problem. This set of data may thus be utilized as an example of training data that allows the calculation of the predicted susceptibility distribution from a phase distribution as part of a solution to the inverse problem.

Figure 5:
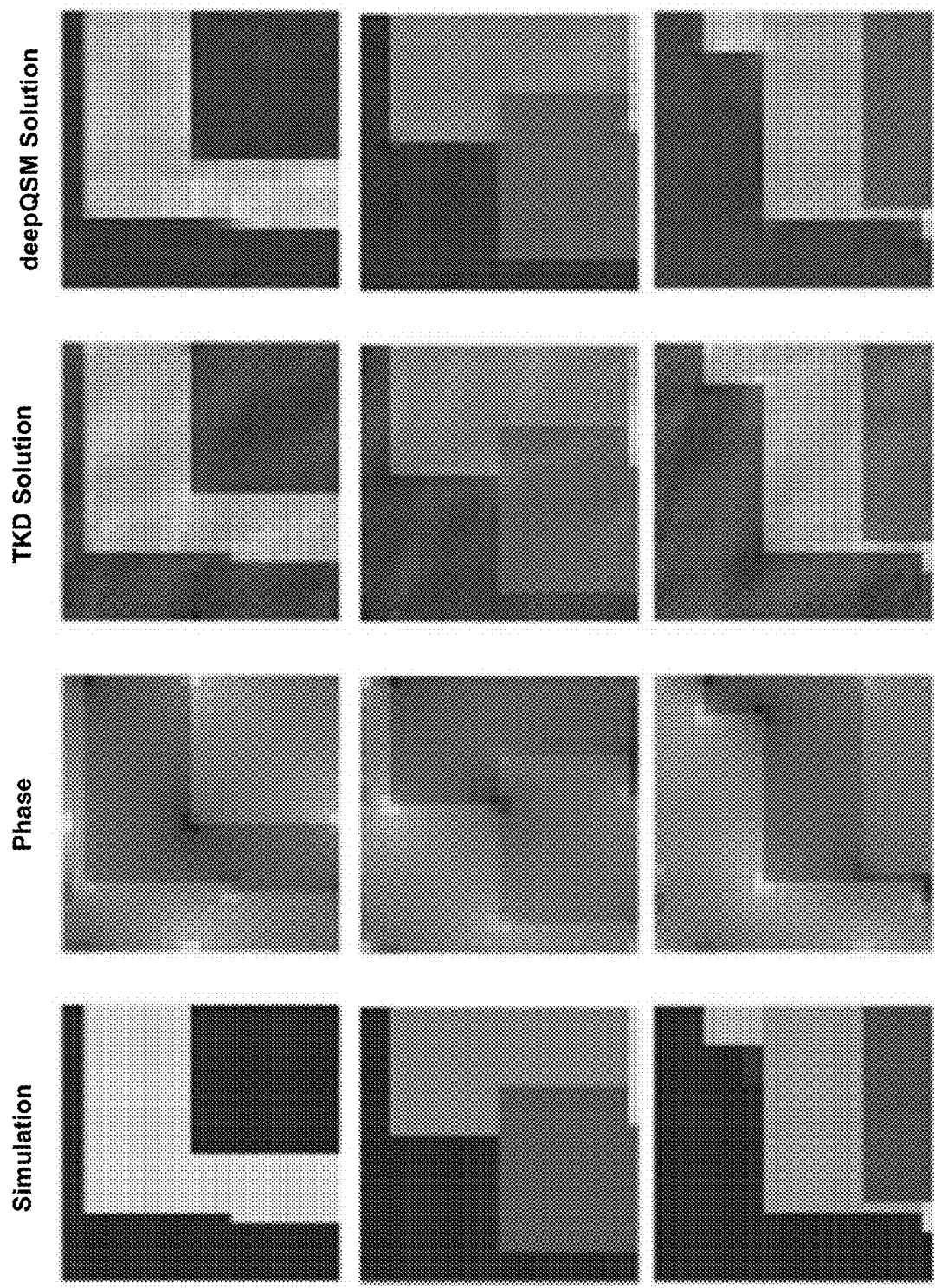
FIG. 5 is a graphical illustration of DeepQSM solutions compared to TKD solutions, in accordance with an aspect of the disclosure.
Figure 6:
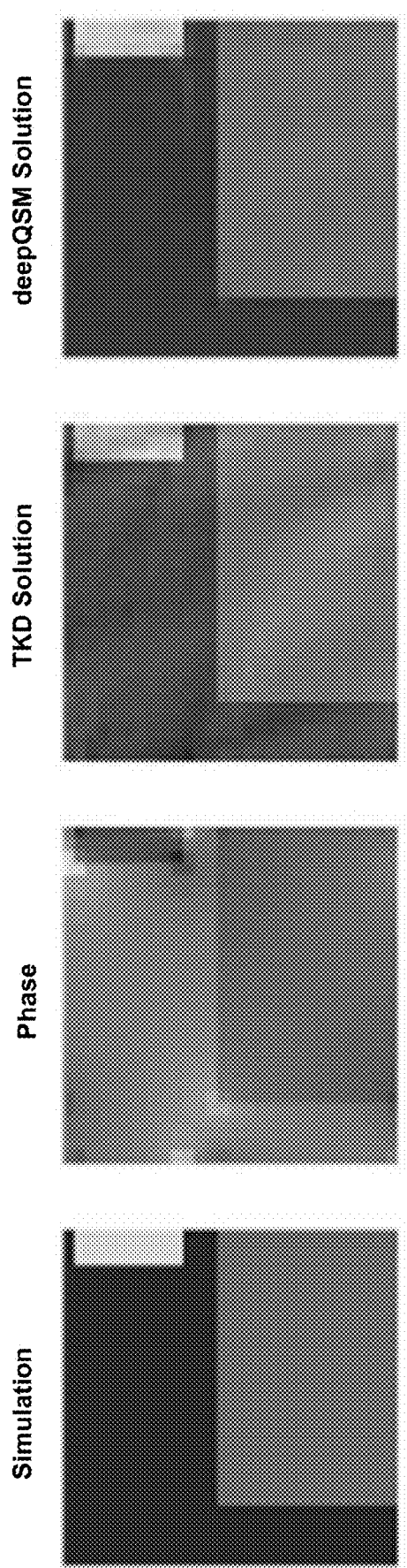
FIG. 6 is a graphical illustration of DeepQSM solutions compared to TKD solutions without measurement noise, in accordance with an aspect of the disclosure.
Figure 7:
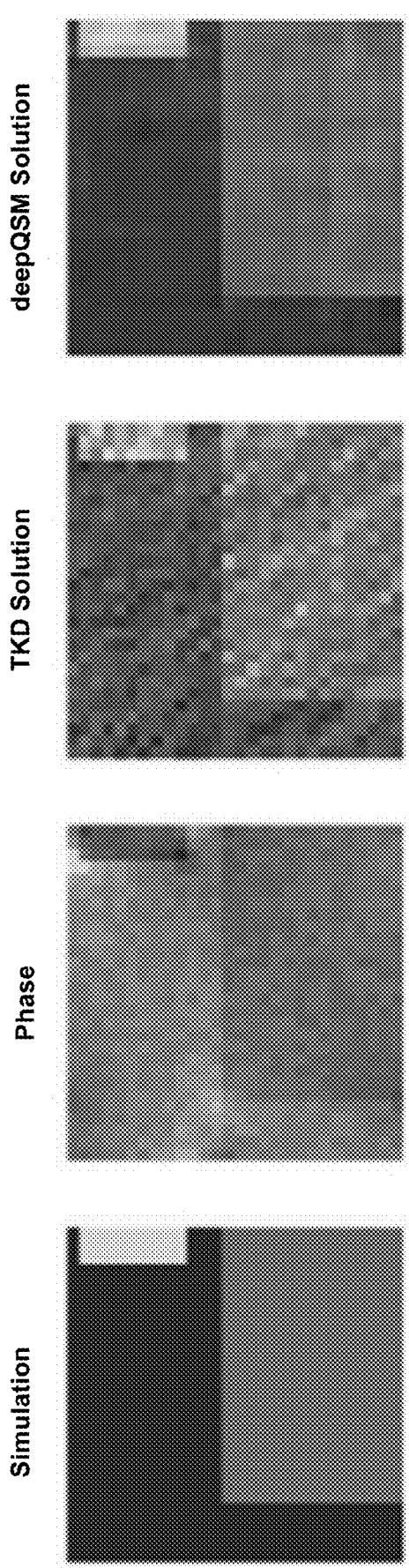
FIG. 7 is a graphical illustration of DeepQSM solutions compared to TKD solutions with measurement noise, in accordance with an aspect of the disclosure.

FIG. 5 is a graphical illustration of DeepQSM solutions compared to TKD solutions, in accordance with an aspect of the disclosure. As shown in FIG. 5, sets of simulated susceptibility distribution data are shown in the first column, with corresponding phase distribution data in the second column. The last two columns compare the conventional "TKD solution" with the DeepQSM solutions obtained in accordance with the aspects described herein. Another example of the training and prediction phase data, which compares the TKD and DeepQSM solutions, is shown in FIG. 6. As shown in FIGS. 5 and 6, the TKD solution performs well in a noise-free environment (i.e., in the absence of measurement noise). However, the graphical illustration shown in FIG. 7 provides another example in which the phase distribution data includes measurement noise, which is a more realistic example. As shown in FIG. 7, the advantages of the DeepQSM aspects versus the conventional TKD solutions are highlighted and, in particular, it is shown in FIG. 7 that the DeepQSM solution provides a more noise robust deep learning inversion.

Due to the ill-posed nature, the inversion of the field-to-source problem is considered the most "difficult" (e.g., most processor-intensive) step in the QSM processing. The QSM pipeline includes additional steps, however, such as unwrapping and background field correction. Current approaches to solving these steps utilize separate algorithms before the inversion, leading to an accumulation of errors, as each of these individual processing steps are dependent upon one other. To overcome these issues, aspects described herein advantageously utilize a deep learning approach to QSM, thereby enabling the integration of these processing steps into the learning framework. In doing so, the aspects described herein effectively render the whole solution as a single, fast matrix multiplication.

In an aspect, this approach utilizes convolutional neural networks or any other suitable, similar machine learning algorithms to predict the underlying susceptibility distribution from MRI phase data, thereby solving an ill-posed inverse problem. This provides the advantages of a fast, accurate, and robust solution of the QSM inversion, even when data associated with only one orientation is available. Further in accordance with such aspects, spatial structure is incorporated into the regularization problem, and therefore the QSM techniques provide high quality reconstructions that, in contrast to the standard techniques, do not suffer from smoothing or noise amplification.

Figure 8:
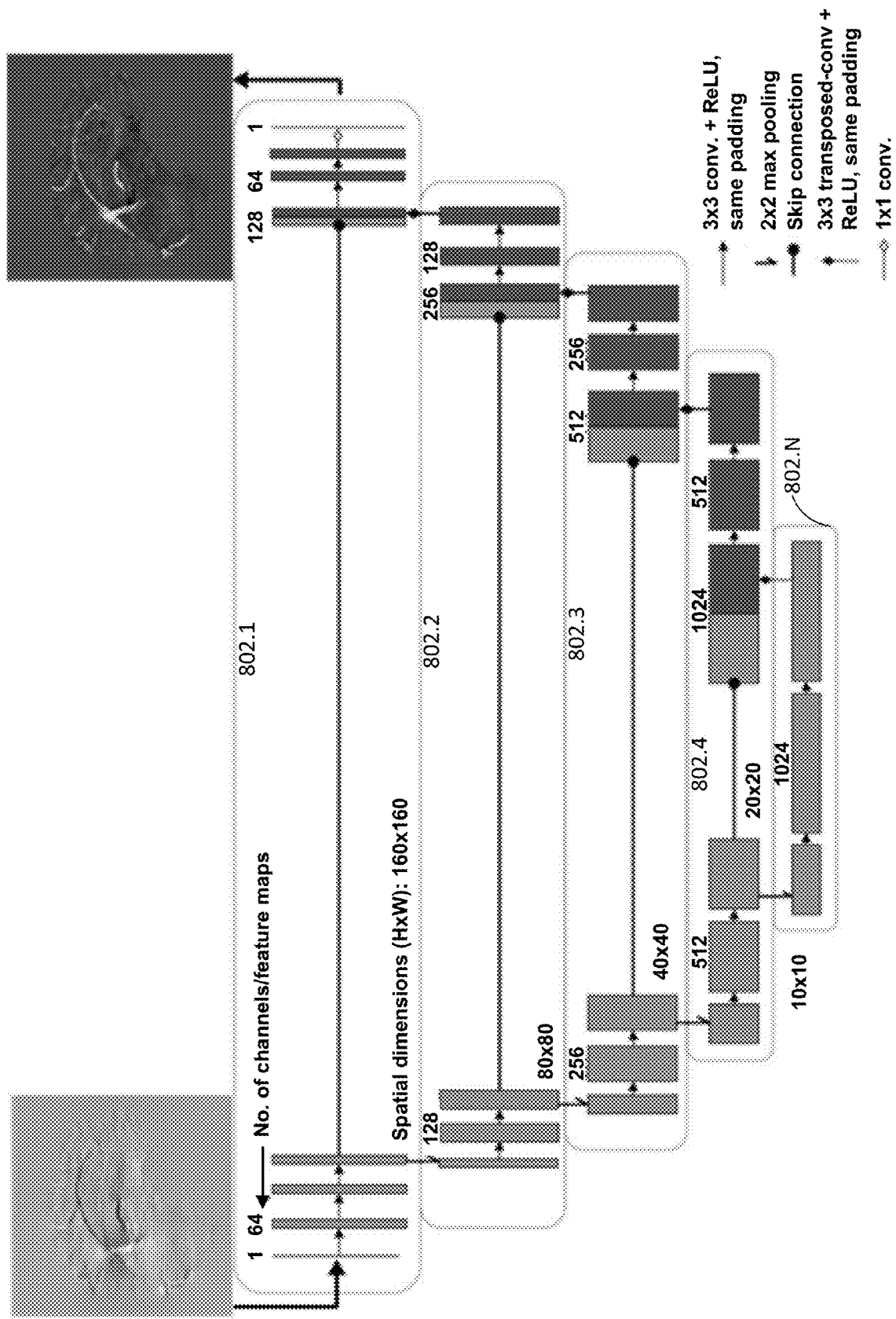
FIG. 8 is a graphical illustration of an example DeepQSM architecture based on U-NET, in accordance with an aspect of the disclosure.

FIG. 8 is a graphical illustration of an example DeepQSM architecture based on U-NET, in accordance with an aspect of the disclosure. The U-NET architecture is a convolutional neural network that was developed for biomedical image segmentation at the Computer Science Department of the University of Freiburg, Germany. The network is based on the fully convolutional network, and its architecture was modified and extended to work with fewer training images and to yield more precise segmentations. As shown in FIG. 8, a QSM method is illustrated utilizing a fully convolutional neural network (e.g., DeepQSM). Thus, the DeepQSM architecture as shown and described with reference to FIG. 8 may be identified with one or more processors (or portions thereof), computer networks, hardware, and/or software components that form a fully convolutional neural network.

To provide an illustrative example, the DeepQSM architecture as shown in FIG. 8 may be based upon one or more U-NET architectures. Of course, these U-NET architectures may be modified, as necessary, depending upon the particular application. This particular type of architecture has been shown to be efficient handling inverse problems (see, e.g., Jin et al. "Deep Convolutional Neural Network for Inverse Problems in Imaging," IEEE Trans. Image Process. 26, 4509-4522 (2017) or Ronneberger et al. "U-Net: Convolutional Networks for Biomedical Image Segmentation," in Medical Image Computing and Computer-Assisted Intervention—MICCAI 2015 234-241 (Springer, Cham, 2015)).

In various aspects, the example DeepQSM architecture may include additional or alternative components not shown in FIG. 8 for purposes of brevity. For example, the example DeepQSM architecture may be generally divided into any suitable number N of functional blocks 802.1-802.N. Each one of these functional blocks 802 may, in turn, include one or more computing devices and/or components, networks, network interface devices, displays, storage media, etc., within the overall neural network or other suitable architecture in which the machine learning algorithms are implemented. In accordance with these aspects, one or more processors identified with one or more of the functional blocks 802.1-802.N may perform the machine learning algorithms by executing instructions stored on one or more suitable storage media (e.g., a non-transitory computer-readable storage medium such as a hard disk or other suitable computer-readable memory). In any event, the functional blocks 802.1-802.N may realize the DeepQSM functions of the aspects described herein.

To provide an illustrative example of the overall operation of the DeepQSM aspects as described herein, the magnetic resonance scanner as discussed with reference to FIG. 1 may generate one or more control signals (or receive one or more control signals from other portions of the magnetic resonance scanner) that result in the acquisition of MRI phase data of sample tissue for a particular three-dimensional orientation. The MRI phase data may, once acquired, be stored in any suitable format and in any suitable type of storage medium. For instance, the MRI phase data may be stored as one or more data files in a memory location that is accessible by the DeepQSM architecture as described herein.

Moreover, the one or more processors associated with the functional blocks 802.1-802.N may likewise generate one or more control signals in response to user input, in response to the execution of computer-readable instructions, and/or upon accessing or reading the acquired and stored MRI phase data. The control signals generated by the one or more processors may thus result in the DeepQSM architecture accessing one or more simulated susceptibility distributions, which may also be stored in a suitable storage medium as one or more data files. The DeepQSM architecture, and in particular one or more of the functional blocks 802.1-802.N may thus generate a respective set of phase distributions from the set of simulated susceptibility distributions using a unique forward solution, train a model using the set of simulated susceptibility distributions and the respective set of phase distributions, with the model representing a learned solution to an ill-posed field-to-source inversion problem. Upon solving the ill-posed field-to-source inversion problem in accordance with the learned model to predict an underlying magnetic susceptibility distribution of the tissue using the MRI phase data, the solutions (e.g., one or more output images) may likewise be stored as one or more data files in a memory location that may be accessed and subsequently viewed, when desired, by appropriate medical personnel. The various computing acts performed by the functional blocks 802.1-802.N may be in response to any combination of user input and/or control signals that are automatically generated in response to the occurrence of certain events, e.g., the completion of MRI phase data acquisition and/or storage of the MRI phase data.

As shown in FIG. 8, aspects include the DeepQSM architecture receiving an image of size M×N. This act of receiving the image may include, for example, retrieving image data that is stored in an appropriate storage medium (not shown) and/or data obtained via a magnetic resonance apparatus, such as magnetic resonance apparatus 5, for example, as shown and described herein with reference to FIG. 1. Moreover, the DeepQSM technique further includes generating and/or outputting an image of size M×N. This step may include, for instance, storing the generated image in an appropriate storage medium (not shown) and/or transmitting data representative of the generated image to another computing device (e.g., the magnetic resonance apparatus 5). The architecture as shown in FIG. 8 is but one example of a computing architecture that may be implemented to perform the DeepQSM technique as described herein, and is shown by way of example and not limitation. To provide an illustrative example, aspects include implementing the DeepQSM using any suitable type of general-purpose programming language (e.g., Python) in accordance with any suitable type of machine learning framework (e.g., Tensorflow). Continuing this illustrative example, aspects include training the DeepQSM data using any suitable number and/or type of processors, such as one or more graphical processing units (GPUs), for instance, to execute a large number of simulated examples (e.g., greater than 100,000) as discussed herein, for data of any suitable spatial dimensions.

For example, the data shown in FIG. 8 was determined using the DeepQSM technique based on a U-NET architecture in conjunction with Python v3.6, Tensorflow v1.320, and an Nvidia Tesla K40c GPU to execute 100,240 simulated examples of size 160×160, at a batch size of 64 for 20 epochs in 15 hours. In other words, the DeepQSM architecture shown in FIG. 8 uses a 160×160 image as input data. Moreover, the network example shown in FIG. 8 includes various convolutions, padding, and pooling steps as indicated by the flow and legend shown in FIG. 8. In particular, the DeepQSM architecture shown in FIG. 8 uses 3×3 convolutions with the same padding, 2×2 pooling on one side, and 3×3 up convolutions on the other side. In an aspect, the transposed convolutions undo the pooling operation, and skip connections are used for residual learning. Moreover, aspects include the final convolution being 1×1 to reduce the feature maps to 1 and to achieve an M×N output image. Again, these steps are shown by way of example, and the DeepQSM architecture aspects described herein may utilize any suitable number of convolutions and/or pooling on either side to achieve the desired results.

Figure 9:
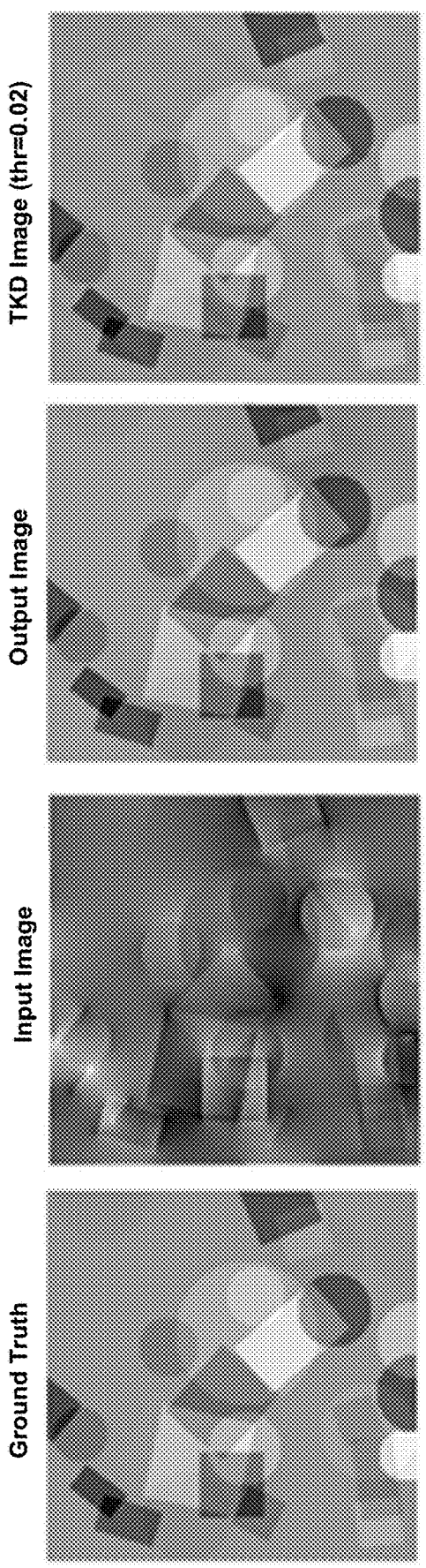
FIG. 9 is a graphical illustration of DeepQSM performance on simulated data, in accordance with an aspect of the disclosure.

In an aspect, the DeepQSM system may be trained on synthetic data (e.g., a simulated dataset) including any suitable number, combination, and/or type of basic geometric shapes such as squares, rectangles, circles, etc. Moreover, the simulated dataset used for training may include shapes of any suitable size and/or patterning. For instance, the simulated dataset may include shapes of a random size, occurrence, overlap, and/or random susceptibility value. In an aspect, the spread of the intensities may be simulated to resemble the spread of QSM images. An example of such simulated data is shown in FIG. 9. With reference to FIG. 9, the example simulated data was convolved with the QSM dipole kernel and white Gaussian noise having a signal-to-noise ratio (SNR) of 20 dB, which was added to generate tissue phase data. With continued reference to FIG. 9, the DeepQSM performance on simulated data is illustrated in further detail. For instance, dataset representative of image 'A' corresponds to simulated susceptibility distribution, whereas the dataset representative of input image 'B' corresponds to simulated tissue phase data. Moreover, the dataset representative of image 'C' or the output image corresponds to the network prediction (e.g., the output image generated in accordance with the DeepQSM architecture as shown in FIG. 8), and the dataset representative of image 'D' shows a TKD solution for comparison.

With continued reference to FIG. 8, aspects include the DeepQSM architecture, or "network" as referred to herein, not necessarily receiving or accessing MRI image data and still learning a general concept behind the field-to-source inversion for QSM. To provide an illustrative example, to test the network's generalizability, the COSMOS reconstruction from the 2016 reconstruction challenge (see article cited above) was convolved with the dipole kernel to generate tissue phase data. This tissue phase data was in turn used as input to the network to predict the underlying susceptibility distribution (e.g., by generating a corresponding dataset). This susceptibility distribution prediction was then compared with the COSMOS result and a TKD reconstruction. The results were then quantitatively evaluated using three error metrics: root mean square error (RMSE), high frequency error norm (HFEN), and structural similarity index (SSIM).

Figure 10:
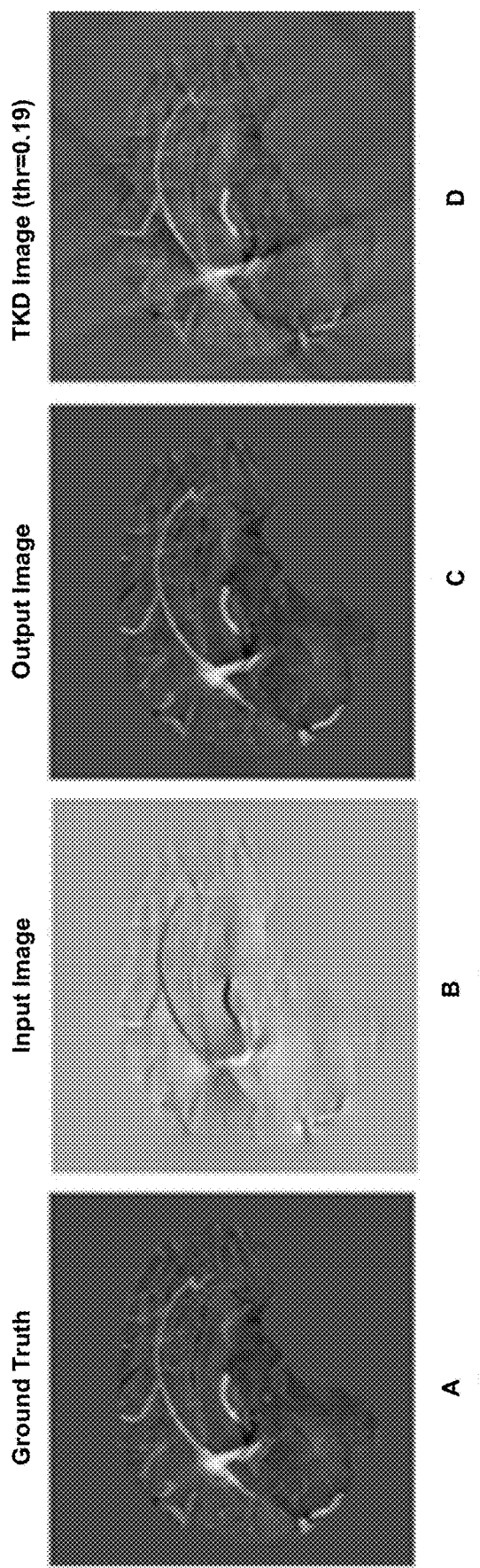
FIG. 10 is a graphical illustration of COSMOS-data performance on simulated data, in accordance with an aspect of the disclosure.

Referring back to FIG. 9, it is observed that the output of DeepQSM on simulated data (the output image in 'C') looks nearly identical to the "ground truth" (the image in 'A'). Thus, the DeepQSM network successfully learned to solve the inverse problem, as further shown in FIG. 10. In particular, FIG. 10 illustrates an example of the DeepQSM aspect described herein (e.g., as shown and described with reference to FIG. 8) in which an output image ('C') has been generated that is nearly identical to the ground truth ('A'). Moreover, unlike the TKD image ('D'), the output image does not suffer from streaking artifacts, as the TKD image uses a truncated version of the dipole kernel (threshold=0.19). In other words, FIG. 10 illustrates an input image ('B') that is generated by applying the dipole kernel to the COSMOS ground truth ('A'). The similarity between the 'A' (ground truth) and 'C' (output image) images thus demonstrates the DeepQSM network's ability to revert the dipole kernel for arbitrary input data. The TKD solution ('D') further illustrates typical streaking artifacts caused by a low truncation threshold.

Figure 11:
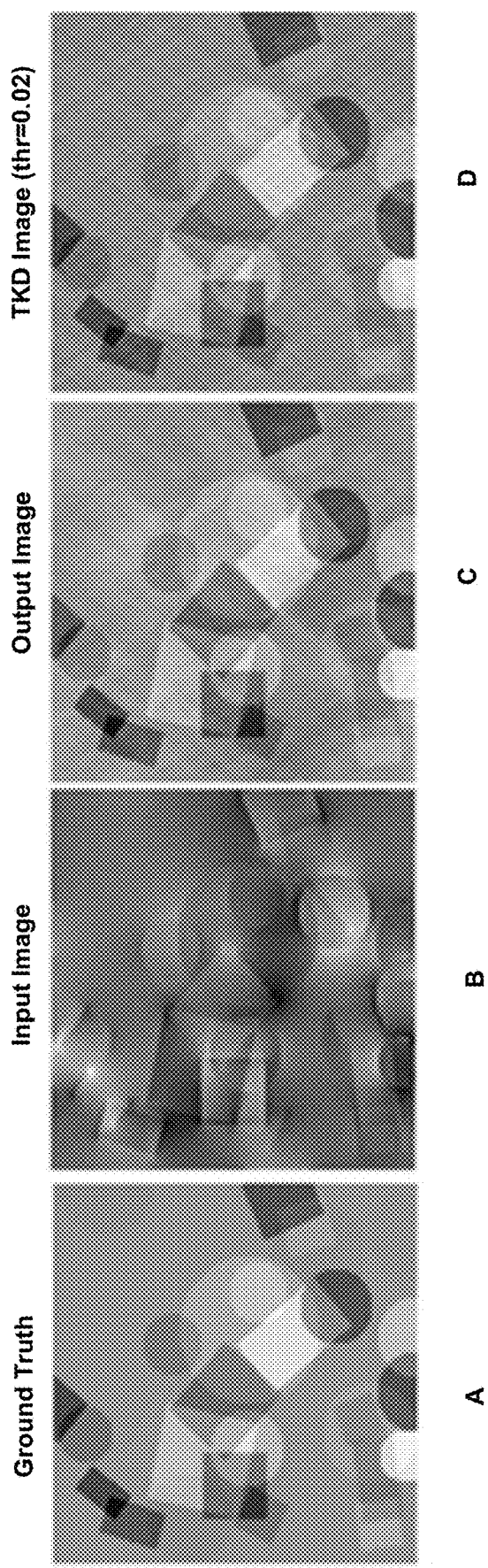
FIG. 11 is a graphical illustration of DeepQSM performance demonstrating noise robustness compared to TKD, in accordance with an aspect of the disclosure.
Figure 12:
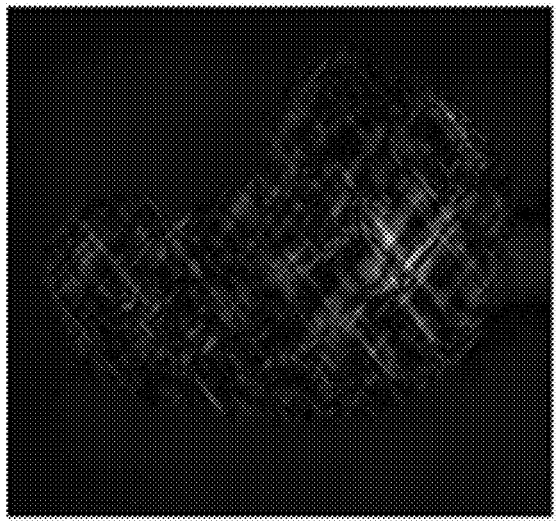
FIG. 12 is a graphical illustration of difference maps comparing ground truths and simulation data for DeepQSM and TKD, in accordance with an aspect of the disclosure.
Figure 12:
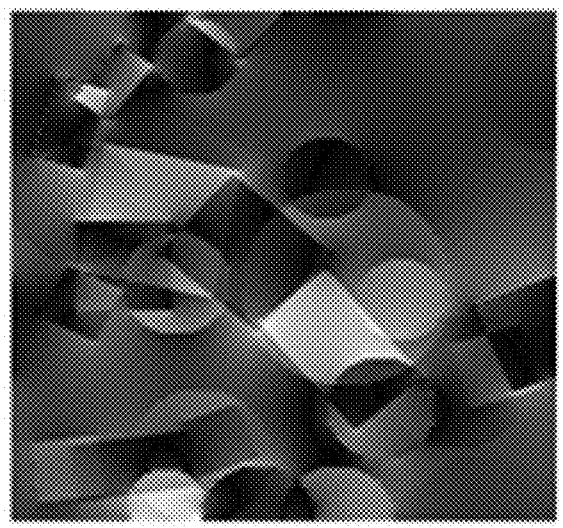
Figure 12:
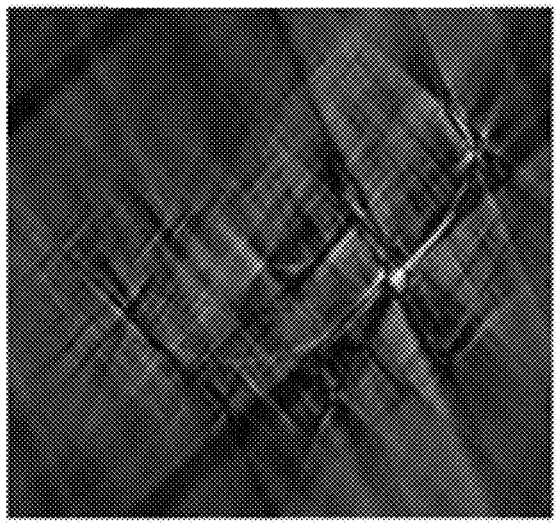
Figure 12:
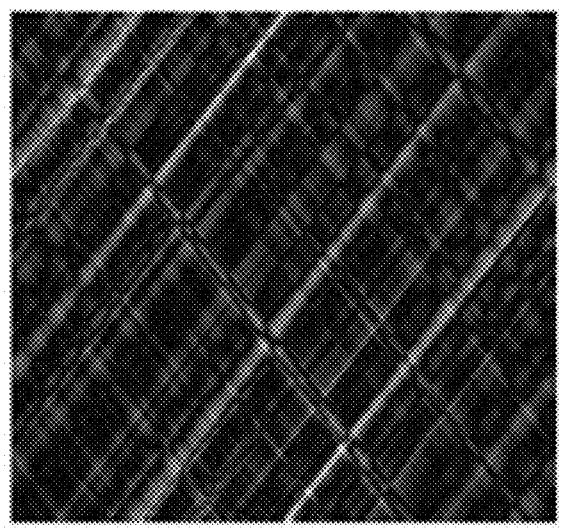

For additional clarity, FIGS. 11 and 12 further demonstrate noise robustness of the DeepQSM network aspects described herein. In particular, the neural network aspects described herein (e.g., such as the DeepQSM architecture as shown and described with reference to FIG. 8) is more robust to noise as compared to the TKD techniques. For example, FIG. 11 illustrates an example output image ('C') that is generated in accordance the DeepQSM architecture aspects described herein, whereas the TKD image ('D') is an example of a dataset generated using the TKD technique with a threshold of 0.02. In this example, Gaussian white noise of 20 dB was introduced to the image after applying the QSM forward problem. As shown in FIG. 10, the output image ('C') includes less streaking artifacts as compared to the TKD-generated image ('D').

Moreover, FIG. 12 illustrates difference maps. Image 'A' corresponds to the difference map of ground truth data for DeepQSM using COSMOS data, whereas image 'B' corresponds to the difference map generated as a result of DeepQSM for simulation data. Image 'C' corresponds to the difference map of ground truth data versus TKD for COSMOS data, whereas image 'D" corresponds to the difference map of ground truth data vs TKD for simulation data. As shown in FIG. 12, noticeable streaking is caused by TKD in images 'C' and 'D.' Thus, FIG. 12 further indicates that DeepQSM reduces the reliance on smoothing regularization, and may better preserve the fine structures within various tissues associated with MRI scans, such as the brain, for instance.

Figure 13:
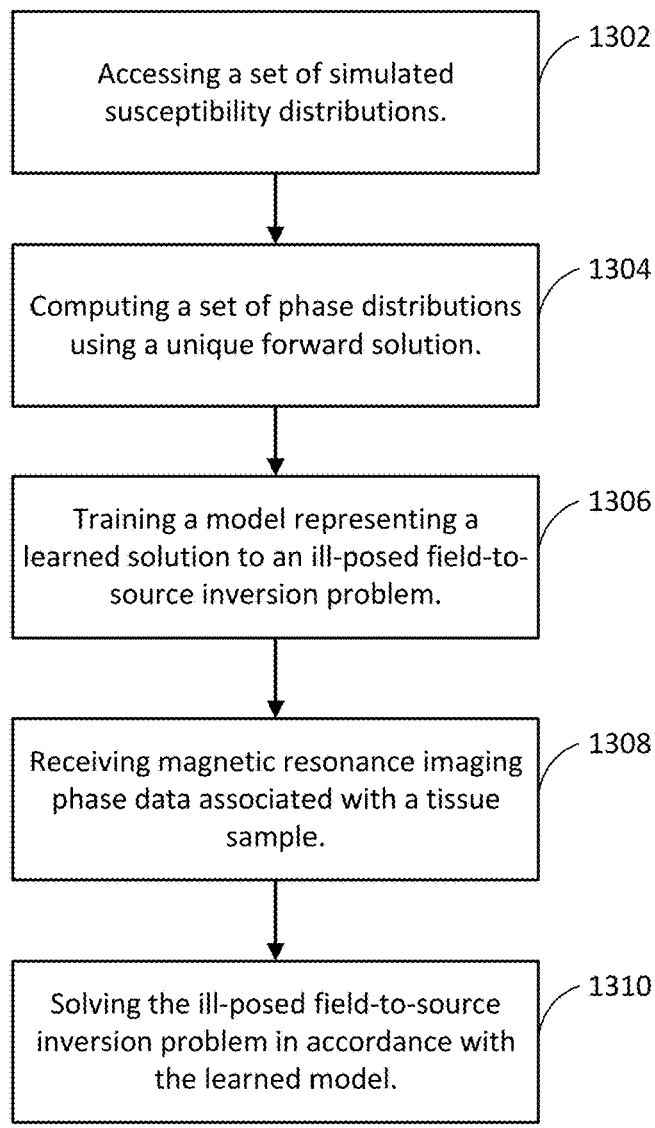
FIG. 13 is an example flow in accordance with an aspect of the disclosure.

FIG. 13 is an example flow in accordance with an aspect of the disclosure. With reference to FIG. 13, the flow 1300 may be a computer-implemented method executed by and/or otherwise associated with one or more processors and/or storage devices. These processors and/or storage device may be, for instance, be associated with a deep convolutional neuronal network, such as the example DeepQSM architecture as shown in FIG. 8, for example. In an aspect, flow 1300 may be performed via one or more processors (e.g., those associated with the DeepQSM architecture as shown in FIG. 8) executing instructions stored on a suitable storage medium (e.g., a non-transitory computer-readable storage medium).

In an aspect, the flow 1300 may describe an overall operation to perform qualitative susceptibility mapping (QSM) to extract a magnetic susceptibility of a tissue by sample-induced magnetization in a static magnetic field, as further discussed herein. Aspects may include alternate or additional steps that are not shown in FIG. 13 for purposes of brevity. For example, as the solved ill-posed field-to-source inversion problem may represent underlying prediction of the magnetic susceptibility distribution, this predicted dataset may be displayed to be viewed by medical personnel.

Flow 1300 may begin when one or more processors receive and/or access (block 1302) a set of simulated susceptibility distributions. This may include, for example, accessing data stored on an appropriate storage medium, as discussed herein with respect to FIG. 8. This may also include accessing data as it is generated and/or prior to the data being stored on a storage medium.

Flow 1300 may further include computing (block 1304) a respective set of phase distributions from the set of simulated susceptibility distributions (block 1320) using a unique forward solution. This may include, for example, obtaining the forward solution by convolving the simulated susceptibility distributions with a dipole kernel to yield corresponding phase distributions, as shown and described herein with reference to FIG. 4.

Flow 1300 may further include training (block 1306) a model using the set of simulated susceptibility distributions (block 1302) and the respective set of phase distributions (block 1304). The model may represent, for example, a learned solution to an ill-posed field-to-source inversion problem.

Flow 1300 may further include receiving (block 1308) magnetic resonance imaging (MRI) phase data associated with a tissue sample. This may include, for instance, receiving phase data acquired via MRI imaging, as discussed herein. Again, in an aspect, the phase data may correspond to a single three-dimensional orientation.

Flow 1300 may further include solving (block 1310) the ill-posed field-to-source inversion problem in accordance with the learned model (block 1306) to predict an underlying magnetic susceptibility distribution of the tissue using the MRI phase data.

Although modifications and changes may be suggested by those skilled in the art, it is the intention of the inventors to embody within the patent warranted hereon all changes and modifications as reasonably and properly come within the scope of their contribution to the art.

What is claimed is:

1. A method for qualitative susceptibility mapping (QSM) to extract a magnetic susceptibility of a tissue by sample-induced magnetization in a static magnetic field, comprising:
    accessing, via a deep convolutional neuronal network, a set of simulated susceptibility distributions;
    computing, via the deep convolutional neuronal network, a respective set of phase distributions from the set of simulated susceptibility distributions using a unique forward solution;
    training, via the deep convolutional neuronal network, a model using the set of simulated susceptibility distributions and the respective set of phase distributions, the model representing a learned solution to an ill-posed field-to-source inversion problem;
    receiving, via the deep convolutional neuronal network, magnetic resonance imaging (MRI) phase data associated with the tissue; and
    solving, via the deep convolutional neuronal network, the ill-posed field-to-source inversion problem in accordance with the learned model to predict an underlying magnetic susceptibility distribution of the tissue using the MRI phase data.

2. The method of claim 1, further comprising:
    displaying an output image representative of the underlying magnetic susceptibility distribution of the tissue.

3. The method of claim 1, wherein the MRI phase data is associated with a single three-dimensional orientation.

4. The method of claim 1, wherein the deep convolutional neuronal network is associated with a U-NET architecture.

5. The method of claim 1, wherein the act of computing the respective sets of phase distributions includes convolving the simulated susceptibility distributions with a dipole kernel to yield corresponding phase distributions.

6. The method of claim 1, wherein the set of simulated susceptibility distributions include one or more geometric shapes and have a spread of intensities to resemble a spread of QSM images.

7. The method of claim 4, wherein the act of solving the ill-posed field-to-source inversion problem includes (i) on one side of the U-NET architecture, using 3×3 convolutions with the same padding and 2×2 pooling, and (ii) on the other side of the U-NET architecture, using 3×3 up convolutions.

8. A deep convolutional neuronal network for qualitative susceptibility mapping (QSM) to extract a magnetic susceptibility of a tissue by sample-induced magnetization in a static magnetic field, comprising:
    a storage medium configured to store a set of simulated susceptibility distributions; and
    one or more processors configured to:
        access the set of simulated susceptibility distributions via the storage medium;
        compute a respective set of phase distributions from the set of simulated susceptibility distributions using a unique forward solution;
        train a model using the set of simulated susceptibility distributions and the respective set of phase distributions, the model representing a learned solution to an ill-posed field-to-source inversion problem;
        access magnetic resonance imaging (MRI) phase data associated with the tissue; and
        solve the ill-posed field-to-source inversion problem in accordance with the learned model to predict an underlying magnetic susceptibility distribution of the tissue using the MRI phase data.

9. The deep convolutional neuronal network of claim 8, further comprising:
    a display configured to present an output image representative of the underlying magnetic susceptibility distribution of the tissue.

10. The deep convolutional neuronal network of claim 8, wherein the MRI phase data is associated with a single three-dimensional orientation.

11. The deep convolutional neuronal network of claim 8, wherein the deep convolutional neuronal network is associated with a U-NET architecture.

12. The deep convolutional neuronal network of claim 8, wherein the one or more processors are configured to compute the respective sets of phase distributions by convolving the simulated susceptibility distributions with a dipole kernel to yield corresponding phase distributions.

13. The deep convolutional neuronal network of claim 8, wherein the set of simulated susceptibility distributions include one or more geometric shapes and have a spread of intensities to resemble a spread of QSM images.

14. The deep convolutional neuronal network of claim 11, wherein the one or more processors are configured to solve the ill-posed field-to-source inversion problem by (i) on one side of the U-NET architecture, using 3×3 convolutions with the same padding and 2×2 pooling, (ii) on the other side of the U-NET architecture, using 3×3 up convolutions.

15. A non-transitory computer-readable medium associated with a deep convolutional neuronal network for qualitative susceptibility mapping (QSM) to extract a magnetic susceptibility of a tissue by sample-induced magnetization in a static magnetic field, the non-transitory medium having instructions stored thereon that, when executed by one or more processors, cause the one or more processors to:
    access the set of simulated susceptibility distributions via the storage medium;
    compute a respective set of phase distributions from the set of simulated susceptibility distributions using a unique forward solution;
    train a model using the set of simulated susceptibility distributions and the respective set of phase distributions, the model representing a learned solution to an ill-posed field-to-source inversion problem;
    access magnetic resonance imaging (MRI) phase data associated with the tissue; and
    solve the ill-posed field-to-source inversion problem in accordance with the learned model to predict an underlying magnetic susceptibility distribution of the tissue using the MRI phase data.

16. The non-transitory computer-readable medium of claim 15, further storing instructions that, when executed by one or more processors, cause the one or more processors to display an output image representative of the underlying magnetic susceptibility distribution of the tissue.

17. The non-transitory computer-readable medium of claim 15, wherein the MRI phase data is associated with a single three-dimensional orientation.

18. The non-transitory computer-readable medium of claim 15, further storing instructions that, when executed by one or more processors, cause the one or more processors to compute the respective sets of phase distributions by convolving the simulated susceptibility distributions with a dipole kernel to yield corresponding phase distributions.

19. The non-transitory computer-readable medium of claim 15, wherein the set of simulated susceptibility distributions include one or more geometric shapes and have a spread of intensities to resemble a spread of QSM images.

20. The non-transitory computer-readable medium of claim 15, wherein the deep convolutional neuronal network is associated with a U-NET architecture, and further storing instructions that, when executed by one or more processors, cause the one or more processors to solve the ill-posed field-to-source inversion problem by (i) on one side of the U-NET architecture, using 3×3 convolutions with the same padding and 2×2 pooling, (ii) on the other side of the U-NET architecture, using 3×3 up convolutions.

* * * * *